US006921397B2

(12) United States Patent
Corcoran et al.

(10) Patent No.: US 6,921,397 B2
(45) Date of Patent: Jul. 26, 2005

(54) FLEXIBLE DELIVERY DEVICE (75) Inventors: Michael P. Corcoran, Oakdale, MN (US); Joseph A. Marino, Apple Valley, MN (US)

(73) Assignee: Cardia, Inc., Burnsville, MN (US)

( * ) Notice: Subject to any disclaimer, the term of this patent is extended or adjusted under 35 U.S.C. 154(b) by 122 days.

(21) Appl. No.: 10/445,512

(22) Filed: May 27, 2003

(65) Prior Publication Data

US 2004/0243143 A1 Dec. 2, 2004

(51) Int. Cl.[7] .............................................. A61M 25/16
(52) U.S. Cl. ...................................................... 604/535
(58) Field of Search ................................ 604/523–536, 604/264, 96.01, 101.01

(56) References Cited

U.S. PATENT DOCUMENTS

| | | | |
|---|---|---|---|
| 3,162,214 A | | 12/1964 | Bazinet |
| 3,674,014 A | * | 7/1972 | Tillander .................... 600/434 |
| 4,955,384 A | * | 9/1990 | Taylor et al. ............... 600/434 |
| 5,381,782 A | | 1/1995 | Delarama et al. |
| 5,477,856 A | | 12/1995 | Lundquist |
| 5,690,120 A | | 11/1997 | Jacobsen et al. |
| 5,776,079 A | | 7/1998 | Cope et al. |
| 5,833,632 A | | 11/1998 | Jacobsen et al. |
| 6,273,876 B1 | * | 8/2001 | Klima et al. ................ 604/264 |
| 6,428,489 B1 | | 8/2002 | Jacobsen et al. |
| 6,682,493 B2 | * | 1/2004 | Mirigian .................... 600/585 |

\* cited by examiner

Primary Examiner—Manuel Mendez
(74) Attorney, Agent, or Firm—Kinney & Lange, P.A.

(57) ABSTRACT

This invention relates to catheter delivery systems, and more specifically, to a tubular device with improved torque and flexure characteristics. The present invention is a tubular device having improved torque and flexure characteristics which uses a series of permanently interlocking independent segments to provide the necessary torque and flexure characteristics.

18 Claims, 7 Drawing Sheets

FLEXIBLE DELIVERY DEVICE

CROSS-REFERENCE TO RELATED APPLICATION(S)

None.

BACKGROUND OF THE INVENTION

This invention relates to catheter delivery systems, and more specifically to a tubular device with improved torque and flexure characteristics.

Catheters, catheter guidewires, and flexible delivery devices have been used for several years to reach and provide treatment at target locations within the human body. For example, occlusion devices that seal heart defects are delivered to the treatment site via catheter, and balloon angioplasty is performed via catheter. Many designs for catheters and guidewires exist. The most important features of a catheter, guidewire, or delivery device are flexibility (so that it can navigate the winding human vasculature), and torque (so a physician can exert force sufficient to steer the device.) Most catheters are made of flexible plastic tubing and come in a variety of lengths and diameters. Most guidewires consist of a metal outer tube comprised of a metal coil coupled with an inner wire.

In practice, physicians generally use a guidewire first to reach the desired location in the body. Upon insertion, the guidewire is tracked with either X-ray technology or ultrasound as the physician maneuvers it to the target location within the patient's body. A catheter can then be advanced over the guidewire after the guidewire has reached the treatment site. The guidewire may be left in place or removed while treatment is accomplished via the catheter.

When the physician navigates to the treatment site, the guidewire must have sufficient flexibility to accomplish the sharp and numerous turns in the body's vasculature. If, however, the guidewire is too flexible, the resistance caused by surface contact with the body's vasculature and the numerous sharp turns will cause the guidewire to buckle and the physician will be unable to reach the treatment site. If the guidewire is too stiff, it will not be able to withstand the demanding angles of the vasculature and likewise will not be able to reach the treatment site. Thus there is a need in the art for a delivery tool that possesses both flexibility and navigability.

BRIEF SUMMARY OF THE INVENTION

The present invention is a medical device, such as a guidewire or delivery device, having improved torque and flexure characteristics. This device uses a series of permanently interlocking independent segments to provide flexibility, pushability, pullability, and necessary torque characteristics.

DETAILED DESCRIPTION

Figure 1:
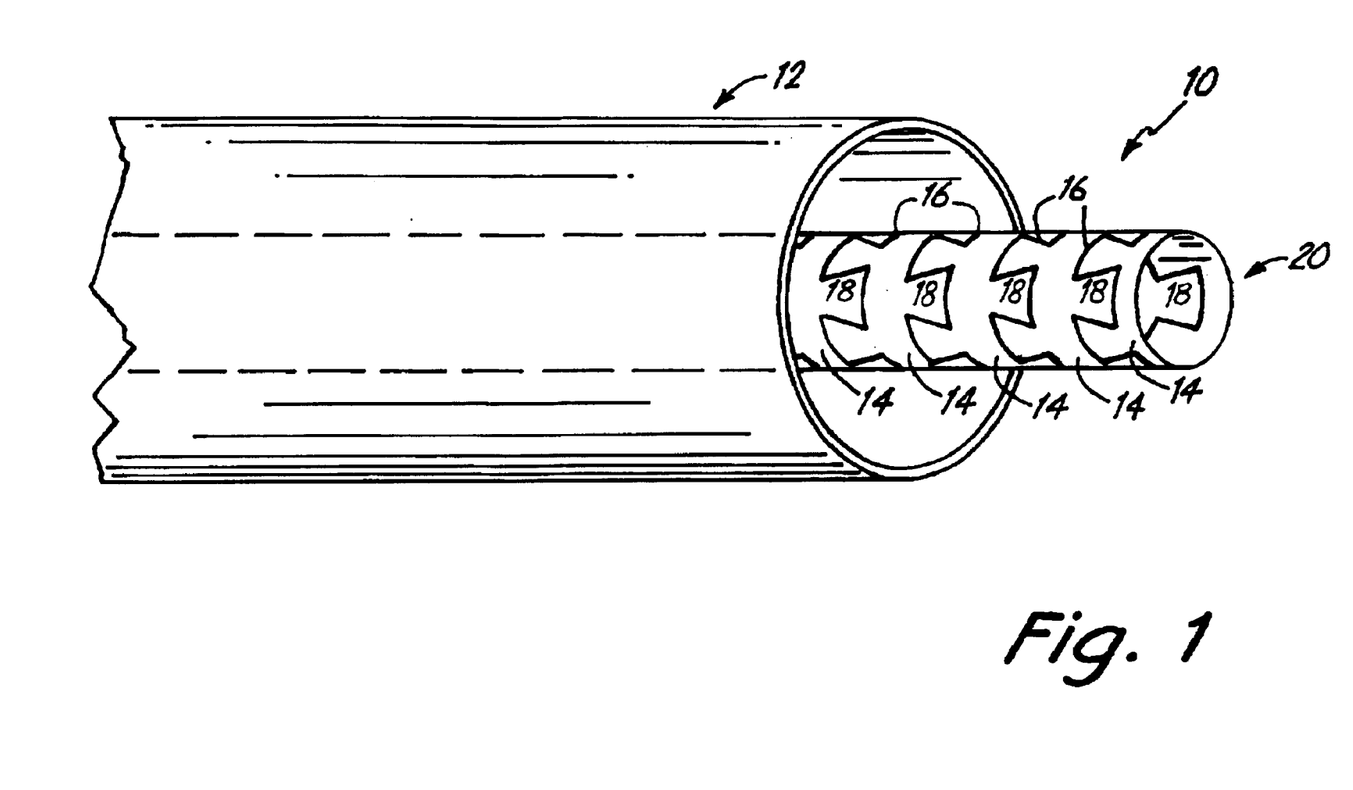
FIG. 1 is a perspective side view of a tubular device extending through a catheter.

FIG. 1 is a perspective side view of a tubular device 10 extending through a catheter 12. The tubular device 10 is comprised of a plurality of independent interlocking segments 14 separated by channels 16. The segments 14 comprise a series of dovetail cut interlocking teeth 18 shaped so that the segments 14 do not disconnect from one another. The segments 14 are separated by channels 16 which can expand axially to give the device 10 increased flexibility or compress axially for increased rigidity. An end segment 20 terminates the device 10 and may be modified to provide an attachment site for additional devices.

The delivery device 10 is constructed of a plurality of segments 14 cut from a single tube. The segments 14 of the delivery device 10 are formed by making a series of cuts the tube. The tube is preferably surgical hypotubing made of stainless steel, nickel titanium, or another suitable material.

The diameter of the tubing varies depending on use. In certain circumstances a tube of tapering or variable diameter may be more effective. For example, if the user prefers that the distal end (the end furthest away from the user) have a very small diameter, the tube may be tapered so that the diameter of the distal end is smaller than that of the proximal end (the end closest to the user). If the device 10 is going to be used in conjunction with a catheter 12, as shown in FIG. 1, the diameter of the device 10 should be similar to the diameter of the catheter 12 so that the device 10 does not have much room to buckle if the device 10 encounters resistance while it is being advanced.

One method of making cuts to form segments 14 is to use a laser. Other suitable cutting methods may also be used to accomplish the cuts, such as using a saw or cutting blade. The method of cutting varies depending on factors such as the size of the tubing and the material used. In an alternate embodiment, the device may be coated with plastic or film when a smooth surface is preferred. The plastic or film must be thin and flexible so that is does not adversely affect the properties of the device 10.

Figure 2:
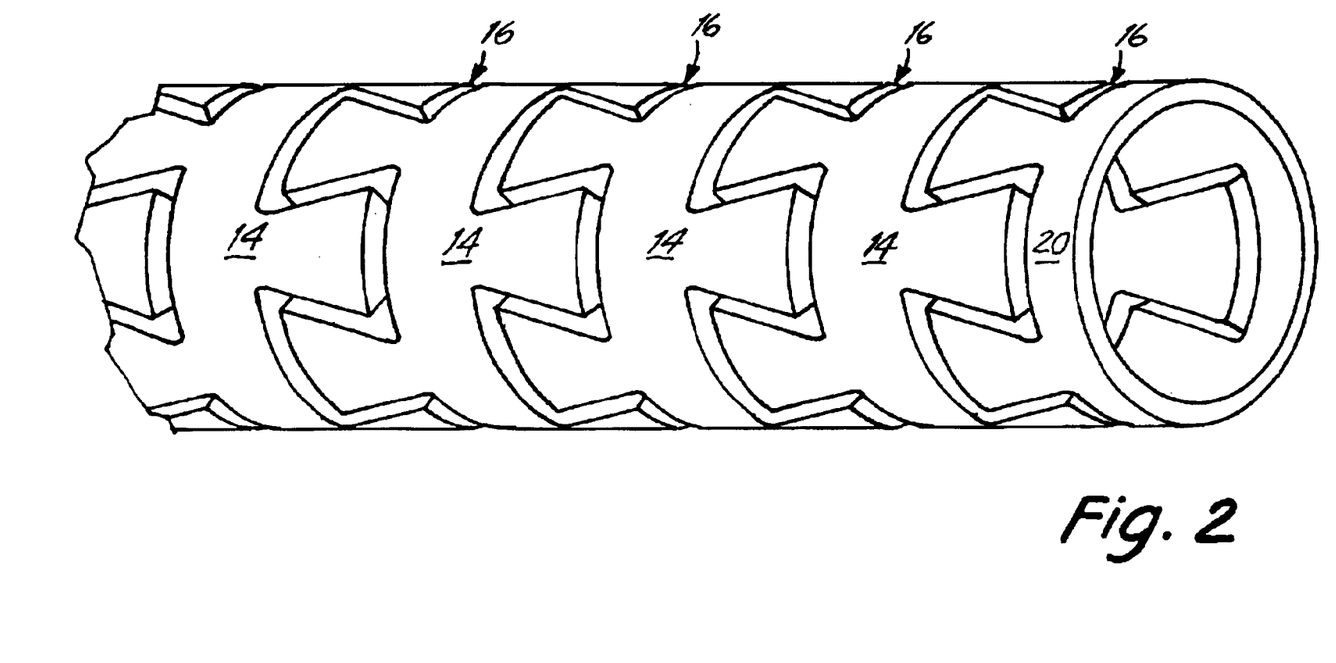
FIG. 2 is a perspective side view of a portion of a tubular device having dovetailed independent interlocking segments.

FIG. 2 shows independent interlocking segments 14, channels 16, and the end segment 20. The segments 14 cannot be axially disconnected because they are defined by a dovetail cut design at each end. The segments 14 are shaped so that they interlock, or mate, with the adjacent segments, allowing flexure but not axial disconnection. In FIG. 2 a dovetail cut is shown but invention is not limited to this cut pattern. Another cut pattern which prevents the segments from axially disconnecting and allows flexure would work also.

By cutting the tube into independent interlocking segments 14 which cannot be axially disconnected because of the cut shape, the segments 14 are able to transmit pushing and pulling forces to adjoining segments 14. The cut design allows the device 10 to transmit axial pushing and pulling forces and also allows transmission of left and right (or counterclockwise and clockwise) twisting forces between segments 14. In addition, as a result of this design, the amount of rigidity automatically adjusts based on the amount of resistance the device 10 encounters.

When the user pushes on the device 10 at the proximal end, as each segment 14 experiences the pushing force, the segment 14 pushes on the distally adjoining segment 14. Therefore, rigidity is created when the segments 14 experience pushing or pulling forces because the segments 14 are locked together with adjoining segments 14 as the width of the channels 22 decreases. The device 10 becomes more rigid as the channels 16 are compressed because the device 10 becomes more like a solid tube as the segments 14 interlock. However, when the segments 14 are not being pushed or pulled or are not experiencing resistance, the channels 16 can expand, the segments 14 do not lock against each other, and the device 10 is more flexible.

Figure 3:
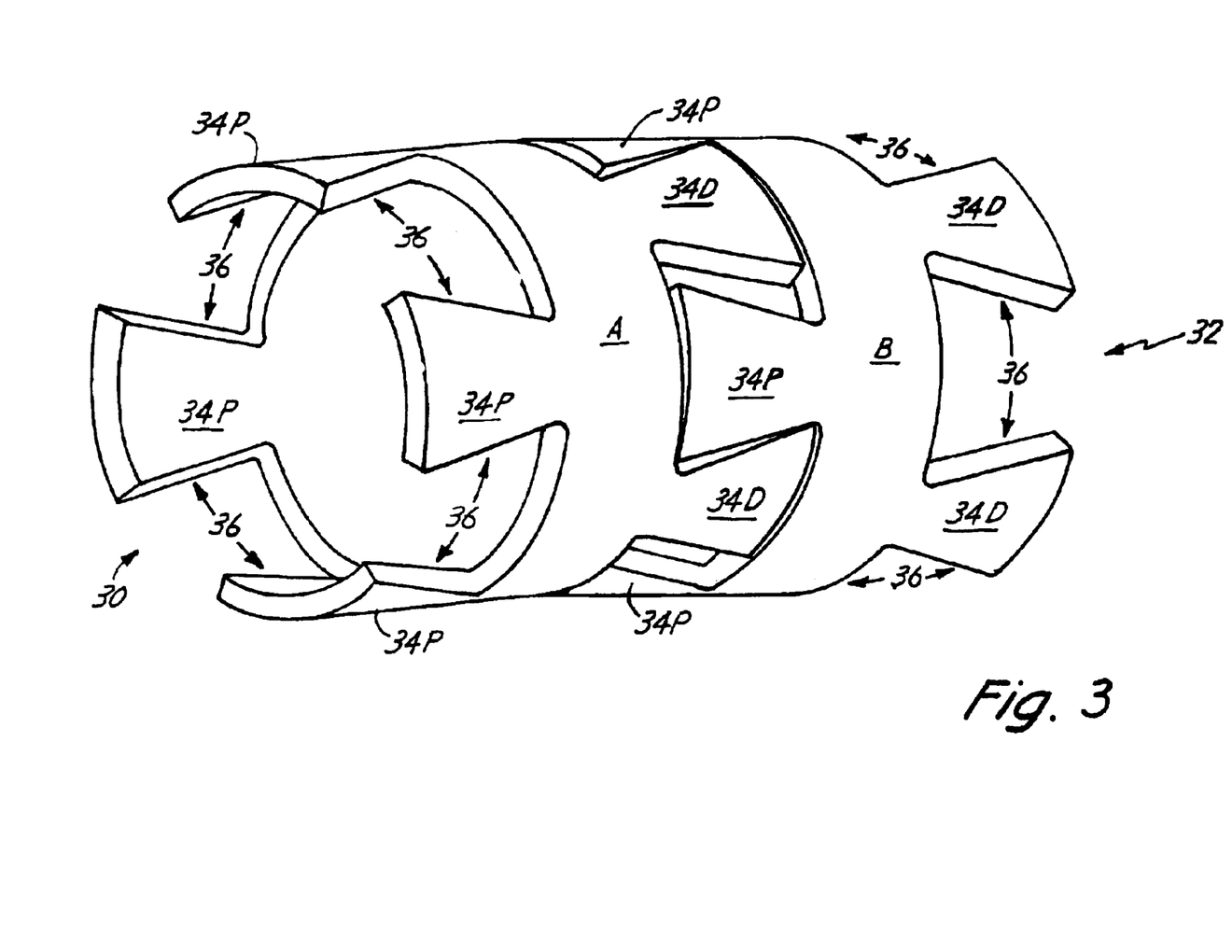
FIG. 3 is a perspective side view of two dovetail cut independent interlocking segments.

FIG. 3 shows an enlarged perspective side view of two segments A, B, each having a proximal end 30 and a distal end 32, as viewed from left to right. The proximal and distal ends 30, 32 are dovetail cut, so that they comprise a plurality of proximal and distal teeth 34P, 34D and grooves 36. The grooves 36 are defined by the teeth 34P, 34D. The distal teeth 34D of segment A fit into the grooves 36 on the adjoining segment B. The distal teeth 34D of segment A widen at the ends and therefore cannot be pulled out of the grooves 36 on the adjoining segment B.

The shape of teeth 34P, 34D and grooves 36 also prevents the segments A, B from rotating laterally, providing torque when needed. The sides of the teeth 34P, 34D and the sides of the grooves 36 provide additional lateral torsion. Because the segments A, B cannot rotate laterally, the pushing or pulling force remains longitudinally directed and the device does not "buckle".

In this embodiment, each segment A, B has four teeth 34D, 34P on each end. If the diameter of the tube used to construct device 10 is increased, the number of teeth 34D, 34P may increase also. In addition, the angle of the dovetail cut may be varied to alter the flexibility of the device.

Figure 4:
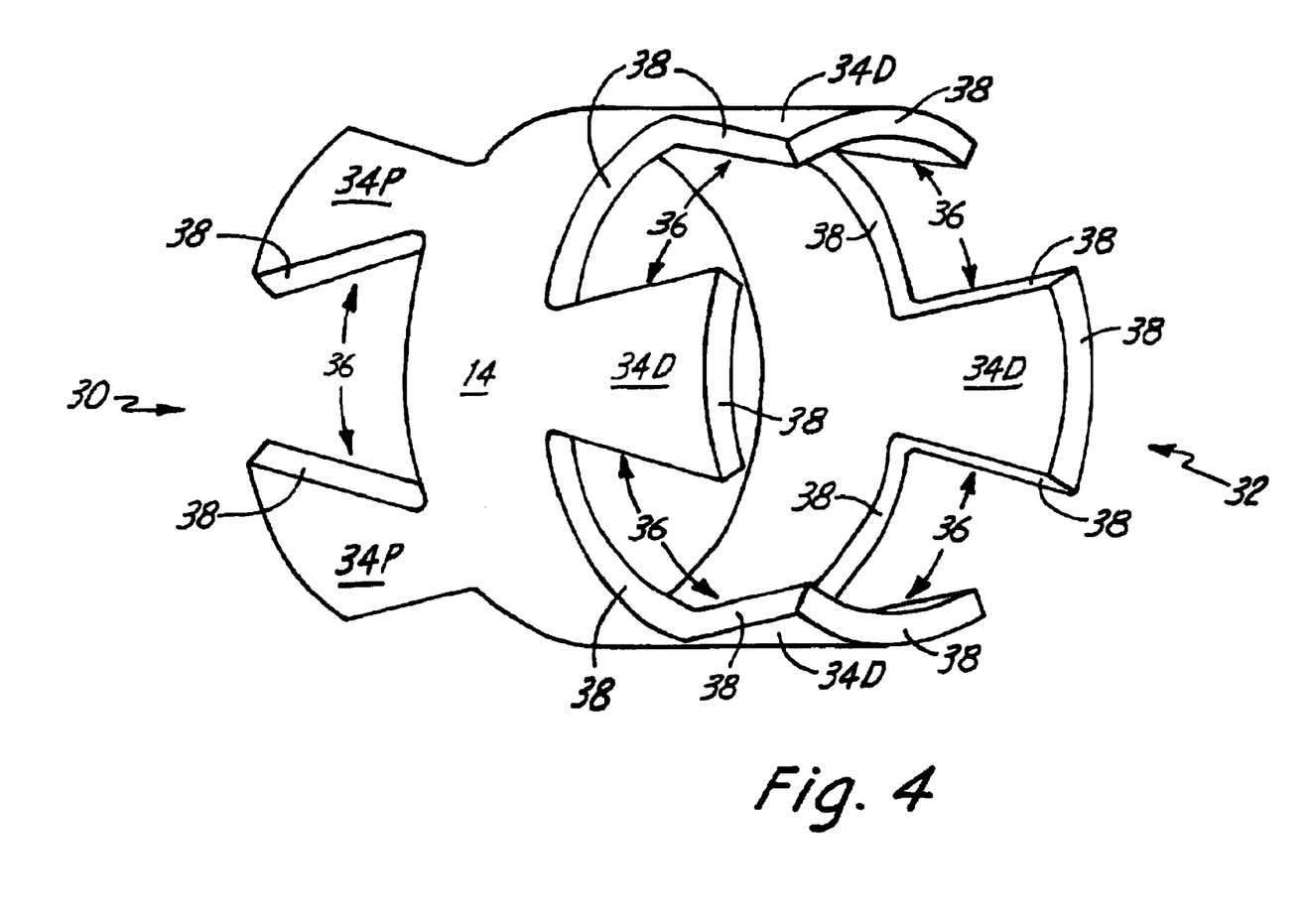
FIG. 4 is a perspective side view of one dovetail cut independent segment.

FIG. 4 is an enlarged perspective view of one segment 14, having a proximal end 30 and a distal end 32, as viewed from left to right. Also shown are proximal and distal teeth 34P, 34D, grooves 36, and mating surface area 38. The teeth 34P, 34D are relatively aligned with the grooves 36 on the opposite end of the segment 14.

By cutting the tube into independent interlocking segments 14 which cannot be axially disconnected because of the cut shape, the segments 14 are able to transmit pushing, pulling, and left and right twisting forces to adjoining segments 14 through their mating surfaces 38. The thickness of the walls of the tube determines the amount of mating surface area 38 between segments 14. As the mating surface area 38 is increased, the pushing, pulling, and torsional strength is increased. However, the flexibility of the device decreases as the mating surface 38 increases. Thus, the thickness of the walls of the tube may also be varied according to user needs.

FIG. 5a through FIG. 5d are enlarged perspective side views of a single tooth experiencing pushing and pulling forces and left and right twisting forces. FIGS. 5a–5d demonstrate how different sides of the teeth engage different sides of the grooves when the tooth experiences either pushing, pulling, or twisting forces.

Figure 5A:
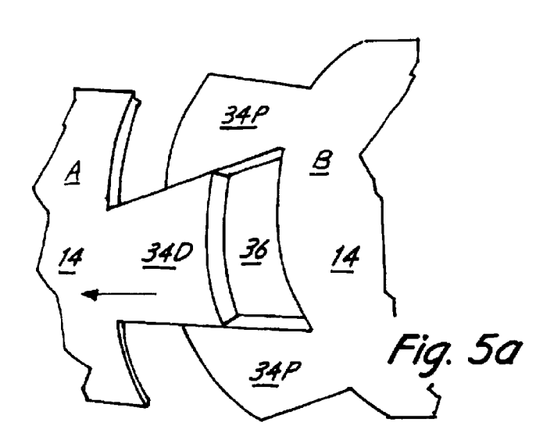
FIGS. 5a-5d are enlarged perspective side views of a tooth of an independent interlocking segment which is experiencing pushing forces, pulling forces and left and right twisting forces, respectively.

In FIG. 5a, a distal end tooth 34D is located in the groove 36 between two proximal end teeth 34P. Shown are two segments A, B, a distal end tooth 34D, two proximal end teeth 34P and a groove 36. The distal end tooth 34D is experiencing a pulling force. The distal end tooth 34D cannot be pulled any further out of the groove 36 because the tooth 34D is too wide at its top to be pulled any further. Thus, a jam fit is created and the pulling force experienced by the first segment A is transferred to the second segment B.

Figure 5B:
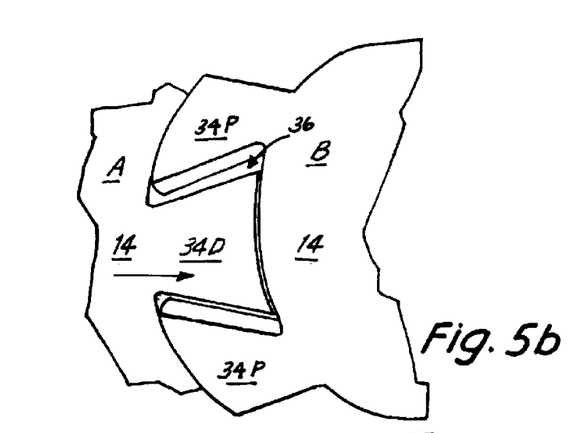

In FIG. 5b a distal end tooth 34D is located in the groove 36 between two proximal end teeth 34P. Shown are two segments A, B, a distal end tooth 34D, two proximal end teeth 34P and a groove 36. The distal end tooth 34D is experiencing a pushing force. The distal end tooth 34D cannot be pushed any further into the groove 36 because the tooth 34D has hit the proximal end of the groove 36. Thus, a jam fit is created and the pushing force experienced by the first segment A is transferred to the second segment B.

Figure 5C:
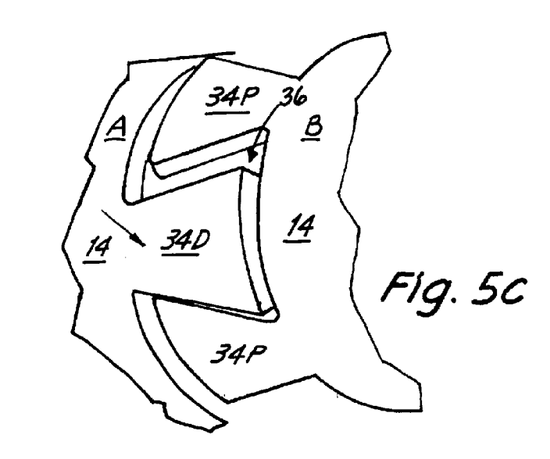
Figure 5D:
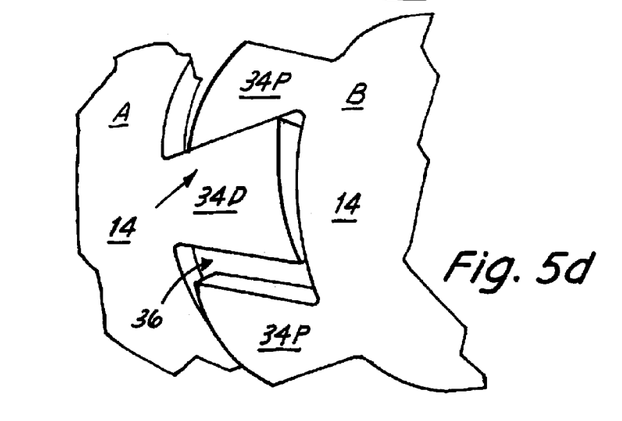

In FIG. 5c a distal end tooth 34D is located in the groove 36 between two proximal end teeth 34P. Shown are two segments A, B, a distal end tooth 34 D, two proximal end teeth 34 P and a groove 36. The distal end tooth 34D is experiencing a left, or counter-clockwise, twisting force. The distal end tooth 34D cannot be rotated any further in the groove 36 because the tooth 34D has been rotated enough to reach the lower end of the groove 36. Thus, a jam fit is created and the counter-clockwise twisting force experienced by the first segment A is transferred to the second segment B.

In FIG. 5c a distal end tooth 34D is located in the groove 36 between two proximal end teeth 34P. Shown are two segments A, B, a distal end tooth 34 D, two proximal end teeth 34 P and a groove 36. The distal end tooth 34D is experiencing a right, or clockwise, twisting force. The distal end tooth 34D cannot be rotated any further in the groove 36 because the tooth 34D has been rotated enough to reach the upper end of the groove 36. Thus, a jam fit is created and the clockwise twisting force experienced by the first segment A is transferred to the second segment B.

Figure 6:
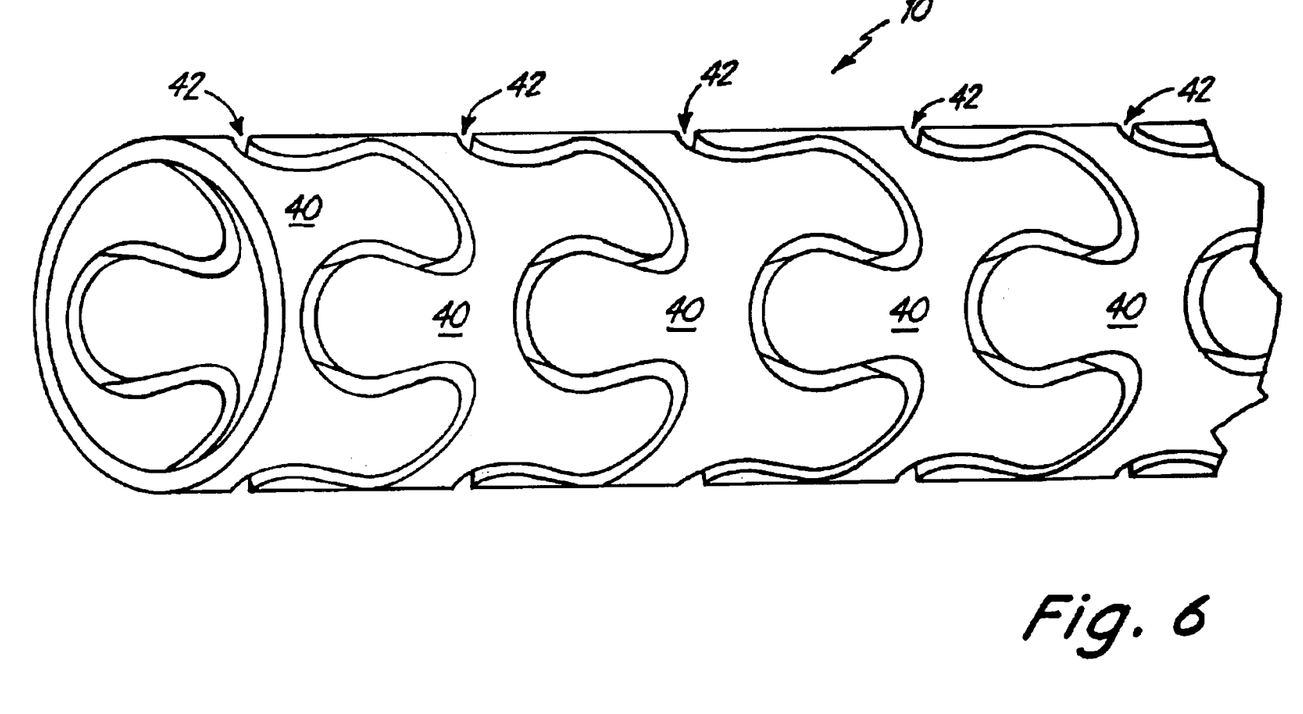
FIG. 6 is a perspective side view of a portion of the tubular device having rounded dovetailed independent interlocking segments.

FIG. 6 is a perspective side view of a portion of a device 10. Shown in FIG. 5 is the device 10, having independent interlocking segments 40 defined by rounded dovetail cut ends, and channels 42. The segments 40 remain axially connected because they are defined by a rounded dovetail cut design on each end. The segments 40 are shaped so that they interlock, or mate, with the adjacent segments, allowing flexure but not axial disconnection. Again, the invention is not limited to this cut pattern; another cut pattern which prevents the segments from axially disconnecting and allows flexure would work also.

As previously mentioned, by cutting the tube into independent interlocking segments 40 which cannot be axially disconnected because of the cut shape, the segments 40 are able to transmit pushing and pulling forces to adjoining segments 40. Rigidity is created when the segments 40 experience pushing or pulling forces because the segments 40 lock together with adjoining segments 40 as the width of the channels 42 decreases. When the segments 40 are not being pushed or pulled or are not experiencing resistance, the channels 42 expand, the segments 40 do not lock against each other, and the device 10 is more flexible.

Figure 7:
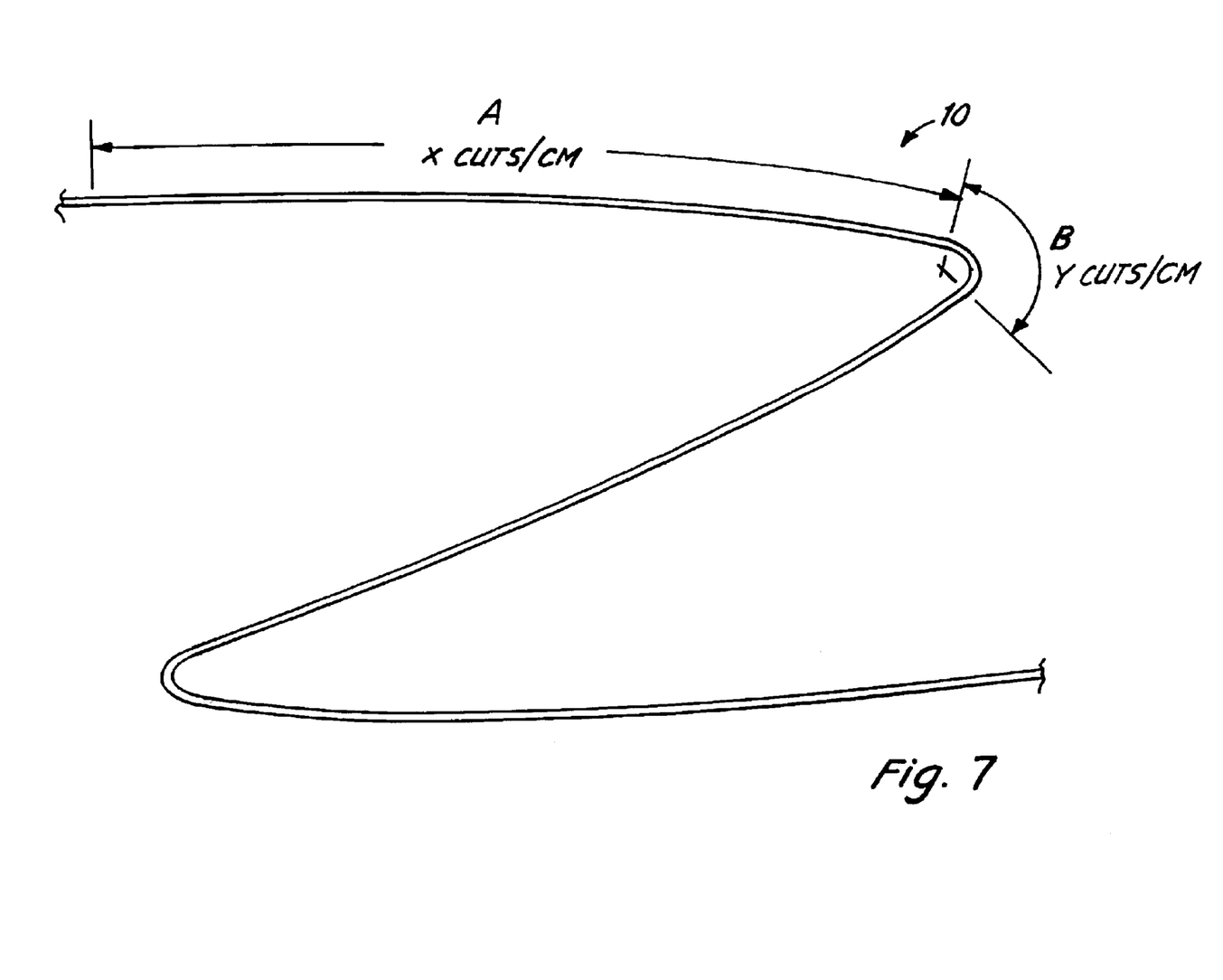
FIG. 7 is a diagram showing how flexure is programable by varying the number of segments per given length.

FIG. 7 is a diagram showing the programmability of the device 10. Shown is the device 10, region "A", and region "B". Region "A" has fewer cuts per centimeter than region "B" and therefore has fewer segments per centimeter. As the number of segments per given length increases, the flexibility of the device 10 increases. Thus, the number of segments per given length can be varied to accommodate certain demands.

For example, when a physician attempts to deliver a cardiac occlusion device to the heart via catheter, the end of the delivery device would be very flexible, ideally. Often, the delivery device must be forced into the heart at an angle, which causes the tissue surrounding the defect to become distorted. If the cardiac tissue is distorted, it is difficult to determine whether the device will be properly seated once the delivery device is removed and the tissue returns to its normal state. If the device is not seated properly, blood will continue to flow through the defect and the device may have to be retrieved and re-deployed. In this situation, it is advantageous to have a delivery device that is very flexible at the end that enters the heart. If the end is very flexible, the amount of distortion can be drastically decreased. The amount of cuts per centimeter can be increased at the distal end of the device 10 to give it the necessary flexibility at the distal end.

Although the present invention has been described with reference to preferred embodiments, workers skilled in the art will recognize that changes may be made in form and detail without departing from the spirit and scope of the invention.

What is claimed is:

1. A guidable tubular device with improved flexibility, the device comprising:
    a tube;
    a plurality of cuts in the tube which separate the tube into interlocking segments, each interlocking segment comprising at least four teeth and at least four grooves, wherein a maximum width of each tooth is approximately equal to a maximum width of each groove and the teeth of one interlocking segment fit into the grooves of an adjacent interlocking segment; and
    wherein each of the plurality of cuts is shaped so that the teeth of one segment cannot be separated from the grooves of an adjacent interlocking segment.

2. The device of claim 1 wherein the plurality of cuts allows a gap to form between each interlocking segment.

3. The device of claim 2 wherein the interlocking segments can be pushed to remove the gap formed between each interlocking segment.

4. The device of claim 1 wherein the plurality of cuts per unit length of the tube is variable.

5. A flexible tubular member for use in a percutaneous delivery system, the member comprising:
    a plurality of tubular interlocking independent segments wherein each segment
    includes:
    a proximal end;
    a distal end; and
    at least four contoured teeth and at least four grooves on both the proximal and distal ends, shaped so that the proximal and distal ends interlock with the proximal and distal ends of adjacent segments, allowing flexing but not axial disconnection, wherein a maximum width of each tooth is approximately equal to a maximum width of each groove.

6. The tubular member of claim 5 wherein the plurality of tubular interlocking independent segments allows a gap to form between each independent segment.

7. The tubular member of claim 5 wherein the interlocking segments can be pushed to remove the gap formed between each interlocking segment.

8. The tubular member of claim 5 wherein the number of segments per unit length of the member is variable.

9. A guidable tubular device for use in a percutaneous delivery system, the device comprising:
    a tubular member;
    a plurality of channels extending circumferentially around and through the tube, creating individual segments of tubing comprising at least four teeth and at least four grooves, wherein a maximum width of each tooth is approximately equal to a maximum width of each groove; and
    wherein the segments of tubing remain interlocked and cannot be disconnected from one another in an axial direction.

10. The guidable tubular device of claim 9 wherein the channels expand to give the device increased flexibility and decrease to give the device increased rigidity.

11. The guidable tubular device of claim 9 wherein the number of segments per unit length of the tubular device is variable.

12. The guidable tubular device of claim 9 wherein the channels comprise a symmetrical fan dovetail cut.

13. The guidable tubular device of claim 9 wherein the channels comprise a symmetrical round dovetail cut.

14. A flexible tubular member for use in a percutaneous delivery system, the member comprising:
    a plurality of modular interlocking independent segments wherein each segment
    includes:
    a proximal end;
    a distal end; and
    a plurality of cuts comprising at least four symmetrical fan dovetail cut contoured teeth and at least four symmetrical fan dovetail cut contoured grooves on both the proximal and distal ends, shaped so that the proximal and distal ends interlock with the proximal and distal ends of adjacent segments allowing flexing but not axial disconnection, wherein a maximum width of each tooth is approximately equal to a maximum width of each groove.

15. The plurality of modular interlocking independent segments of claim 14 wherein the plurality of cuts allow a gap to form between each interlocking independent segment.

16. The member of claim 14 wherein the interlocking segments can compress when pushed to remove the gap formed between each interlocking segment.

17. The member of claim 14 wherein the number of segments per unit length of the member is variable.

18. The member of claim 14 wherein the dovetail cut comprises rounded edges.

* * * * *